United States Patent [19]
Wright

[11] Patent Number: 6,039,176
[45] Date of Patent: Mar. 21, 2000

[54] SURGICAL SUTURE HOLDER

[76] Inventor: John T. M. Wright, 555 S. Downing St., Denver, Colo. 80220

[21] Appl. No.: 09/303,885

[22] Filed: May 3, 1999

[51] Int. Cl.⁷ .................................................. A61B 17/06
[52] U.S. Cl. ............................................... 206/63.3
[58] Field of Search ................... 206/63.3, 380, 206/381, 382, 339

[56] References Cited

U.S. PATENT DOCUMENTS

| | | | |
|---|---|---|---|
| 385,937 | 7/1888 | Lee | 206/63.3 |
| 3,819,039 | 6/1974 | Erickson | 206/388 |
| 5,282,533 | 2/1994 | Holzwarth et al. | 206/63.3 |
| 5,325,975 | 7/1994 | Brown et al. | 211/184 |
| 5,335,775 | 8/1994 | Scanlon et al. | 206/63.3 |
| 5,350,060 | 9/1994 | Alpern et al. | 206/63.3 |
| 5,413,214 | 5/1995 | Schonke | 206/63.3 |
| 5,529,175 | 6/1996 | Brunken | 206/63.3 |
| 5,601,185 | 2/1997 | Behring et al. | 206/63.3 |
| 5,769,214 | 6/1998 | Zatarga | 206/63.3 |
| 5,848,714 | 12/1998 | Robson et al. | 211/170 |

*Primary Examiner*—David T. Fidei

[57] ABSTRACT

A suture holder comprising a prestressed spring secured to extend longitudinally in and laterally through a slot in a bracket in such a way that one side of the spring is available to receive sutures such that the resilient force of the spring retains the sutures in the spring against the bracket is disclosed.

22 Claims, 1 Drawing Sheet

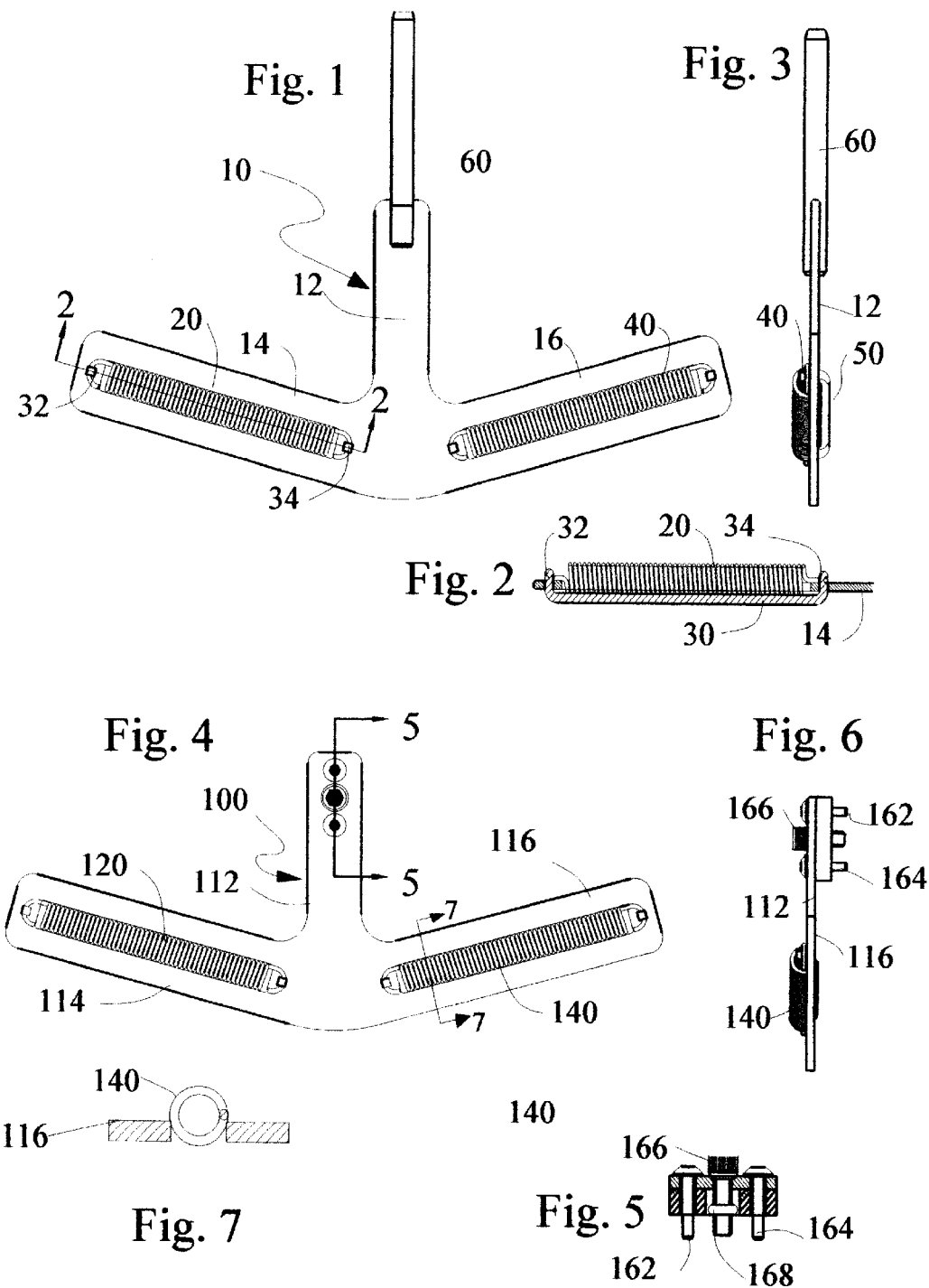

SURGICAL SUTURE HOLDER

FIELD OF THE INVENTION

This invention relates generally to surgery and specifically to devices for holding surgical sutures.

BACKGROUND OF THE INVENTION

Surgical sutures are by their very nature difficult handle and display in a manner that will permit the surgeon quickly and accurately to select the proper suture for the procedure being performed.

The prior art is replete with devices intend to hold or present sutures for shipment, storages and use. Some such devices are designed to ship or store sutures and are no)t suitable for use in the operating room. Other such devices may be used in the operating room but fail to solve all of the problems associated with holding and displaying sutures to make them conveniently available to the surgeon.

U.S. Pat. No. 5,769,214 to discloses a suture pack that appears partially to solve some of the problems in handling sutures. This device is, however, complex and difficult to assemble and use.

U.S. Pat. No. 5,848,714 discloses a different approach wherein each suture is separately packaged and the individual packages are displayed. While this approach has its advantages, it requires handling of packages in addition to the handling of the sutures and may make overall handling of sutures more complicated rather than simpler.

U.S. Pat. No. 5,601,185 discloses a complicated folding device for holding sutures that would tend to clutter the operating room.

U.S. Pat. Nos. 5,529,175 and 5,413,214 disclose suture packages which are compact but which do not display sutures for convenient retrieval in the operating room.

U.S. Pat. Nos. 5,335,775, 5,325,975, and 5,282,533 disclose apparatus for displaying sutures that are bulky and complex and do not offer means for placing the sutures in easy reach of the surgeon during a surgical procedure.

Springs have been used to support sutures. At first glance, a coil spring in which the coils are pre-stressed with a resilient bias toward each other, or can be separated only by a force acting against the spring bias, would seem to present a nearly ideal holder. The suture can be easily inserted into the spring, is firmly held in the spring and can, in concept at least, be easily removed. In practice, however, springs have not been well accepted as suture holders because of the tendency of the sutures to wrap around a coil of the spring and, thus, become extremely difficult to remove from the spring for use in the surgical procedure.

The present invention features the advantages of spring retention of sutures in a manner which solves the previous problems in using springs and also provides a convenient presentation of the sutures adjacent the surgical field.

SUMMARY OF THE INVENTION

The present invention comprises, in a convenient embodiment, a prestressed spring secured to extend longitudinally in and laterally through a slot in a bracket in such a way that one side of the spring is available to receive sutures such that the resilient force of the spring retains the sutures in the spring against the bracket.

In a desired form, the bracket is configured and constructed to support two such springs secured in separate slots in the manner described.

It is an advantageous feature of this invention that mounting means are provided as part of or in association with the bracket to mount the bracket on a surgical appliance such as, by way of example only, a sternal retractor.

In a more specific sense, the surgical suture holder of this invention comprises a bracket constructed of generally planar flat material having a thickness, the bracket being so configured and constructed as to define there through at least one elongate slot having a length and a width and having the depth which is the thickness of the bracket material, a prestressed coil spring having a length and a diameter, the diameter of the spring being slightly less than the width of the slot in the bracket and being greater than the depth of the slot in the bracket and means securing the spring in the slot with one longitudinal side portion of the spring extending outwardly from the surface of the bracket material a distance sufficient for sutures to be inserted between coils of the spring. The bracket, spring and spring securing means are so configured, constructed and assembled as to enable sutures to be inserted between spring coils against bias of one spring coil toward an adjacent coil to removably hold the suture in a position adjacent a surgical operating field for easy selection and removal by the surgeon or surgical assistant.

The invention may optionally comprise means for mounting the suture holder to a surgical appliance.

In a typical preferred embodiment, the spring and bracket are so configured and constructed that the spring extends along the length thereof from the bracket a distance of from $\frac{1}{16}$ inch to $\frac{1}{4}$ inch and the spring securing means extends along the length of the spring adjacent thereto on a side opposite to the side of the spring that extends from the bracket.

In a preferred embodiment, the bracket is so configured and constructed as to define two slots having a length and a width and having the depth which is the thickness of the bracket material, and comprises two prestressed coil springs each having a length and a diameter, the diameter of the springs being slightly less than the width of the slots in the bracket and being greater than the depth of the slots in the bracket and means securing the respective springs in the respective slots with one longitudinal side portion of the respective springs extending outwardly from the surface of the bracket material a distance sufficient for sutures to be inserted between coils of the spring, each spring and spring securing means being so configured, constructed and assembled as to enable sutures to be inserted between spring coils against bias of one spring coil toward an adjacent coil io removably hold the suture in a position adjacent a surgical operating field for easy selection and removal by the surgeon or surgical assistant.

In an exemplary embodiment, the springs and bracket are so configured and constructed that the spring extend along the length thereof from the bracket a distance of from $\frac{1}{16}$ inch to $\frac{1}{4}$ inch and wherein the bracket is constructed of stainless steel plate from $\frac{3}{32}$ inch to $\frac{5}{32}$ inch thick.

BRIEF DESCRIPTION OF THE DRAWING

FIG. 1 is a top plan view of one form of the suture holder of this invention.

FIG. 2 is a partial cross-section of the suture holder taken perpendicular to the plane shown in FIG. 1 along lines 2 2 in the direction of the arrows.

FIG. 3 is a side elevational view of the suture holder of FIG. 2 taken of the right side of the holder as depicted in FIG. 2.

FIG. 4 is a top plan view of an alternative embodiment of the suture holder wherein the spring and bracket structure is the same as shown in FIG. 1 but wherein the mounting means differs from that shown in FIG. 1.

FIG. 5 is a partial cross-sectional view of the suture holder of FIG. 4 taken along lines 5 5 of FIG. 4 in the direction of the arrows, showing in cross-section the mounting means.

FIG. 6 is a side elevation view of the suture holder of FIG. 4 take from the right as shown in FIG. 4.

FIG. 7 is a cross-sectional view taken along lines 7—7 of FIG. 4 showing the relationship of the spring and the edges of the slot in the alternative configuration of FIG. 4.

DESCRIPTION OF THE PREFERRED EMBODIMENTS

The following description is directed to the presently preferred embodiments ot the invention. The invention is not, however, limited to the specific embodiments shown or described. Materials are not critical to the invention in that there are many suitable materials. Stainless steels, titanium, alloys of the same and of other metals are known to be suitable for the manufacture of surgical instruments. Polymeric materials of great strength are available as are resilient polymers. Any material of suitable strength and, in the case of the springs, resiliency may be used. Dimensions, likewise, are not critical. In general, the suture holder may preferable be manufactured to have a maximum width or length of from three to nine inches, but larger or small devices would be within the scope of the invention. Material thicknesses, spring characteristics, etc. are variable and may be selected to obtain maximum mechanical strength and functionality from the materials. At present, stainless steel or comparable alloys are preferred but other metals, alloys and even polymeric materials may be used the latter being especially attractive in the manufacture of disposable products.

Referring first to FIGS. 1, 2 and 3, the major components of the suture holder 10 are a bracket comprising, in a preferred form, three legs 12, 14 and 16, each having proximal and distal ends, the proximal ends being joined together at a common point the distal ends extending therefrom, one or more springs 20 and 40 secured in slots in the bracket and, optionally, mounting structure 60 for mounting the suture holder on a surgical appliance. The suture holder may, for example, be mounted to a sternal retractor for use in open heart surgery, etc. The suture holder may, of course, comprise only one leg comprising a spring holding portion. Likewise, the holder may comprise two legs, one portion for mounting the holder and another portion for holding the spring.

The bracket is so configured and constructed as to define an elongate slot in one or more of the legs, the slot having a length, width and depth. The depth of the slot is, of course, the thickness of the bracket which is generally from about ³⁄₃₂ to ⁵⁄₃₂ inch, but which may be of any convenient thickness. The spring 20, which has a length and diameter, is secured to extend longitudinally in the slot and lie laterally in the slot. The spring and slot are so configured and constructed that the slot is slightly wider than the diameter of the slot so the spring can expand and contract in the slot. A spring mount bar 30, best shown in FIG. 2, having hooks 32 and 34 extending through the slot is welded or otherwise affixed to the bracket. In a preferred embodiment, the spring and bracket are so configured and constructed that the spring extends along the length thereof from the bracket a distance of from ¹⁄₁₆ inch to ¼ inch. The spring 20 is provided with ring end portions 22 and 24 that are received, respectively, on hooks 32 and 34 of the spring mount bar 30. The bar rests against one side of the spring. This relationship of the bar resting against the spring is very important. Springs have not been found to be satisfactory suture holders in the past because the sutures, being very fine and flexible, wrap around one or more coils of the spring and cannot be readily removed. Even the smallest space between the spring mount bar and the spring would permit this to occur. Consequently the bar must touch the spring. Similarly, if the spring is allowed to bow, the sutures may wrap around the spring and/or become snarled on the spring coils. Thus, and important function of the spring bar is to prevent the spring from flexing. The spring, bracket, slot and spring mount bar are so configured and constructed that the spring lies latterly in the slot with a first side extending from the bracket a distance, e.g., ⅛ to ¼ inch, sufficient to receive sutures. In its unstressed condition, the coils of the spring preferably lie against each other. In the suture holder, the spring is stretched very slightly to leave a small space of a few ten thousands or thousands of an inch between the coils. A The spring 40 is likewise secured by a securing bar 50, best shown in FIG. 3, in the same manner in the slot in the bracket portion 16 of the suture holder 10.

A rod 60 is optionally welded or attached to the bracket to permit the bracket to be easily mounted to a surgical appliance. Any mounting means may be used, the rod being a convenient structure for being clamped to a surgical appliance.

The suture holder of FIGS. 4. 5 and 6, to which reference is now made, is identical to the suture holder just described except as to the means for mounting the suture holder to a surgical appliance. Specifically, the bracket, spring, slot and securing bar structures are identical.

The bracket 100 of FIGS. 4, 5 and 6 comprises legs 112, 114 and 116, the legs 114 and 116 having a slot there through, all as described in reference to bracket 10. The springs 120 and 140 are, however, secured by suitable hooks or fasteners such that the spring rests against the edge of the slots in the frame. This relationship is shown in FIG. 7. With spring 140 resting against the edges of the slot in leg 116, it is impossible for the suture to wrap around a coil and, likewise, it is impossible for the spring to bow when sutures are placed therein.

Referring specifically to the mounting structure shown in FIGS. 4, 5 and 6, the leg 112 is configured and constructed to define three passages aligned longitudinally along the length of leg 112 proximate the distal end to that leg, the proximal end thereof joining the proximal ends of legs 114 and 116. A mounting plate 160 that defines three passages that can be aligned with the passages in leg 112 is secured to or, in use, retained on leg 112 with the respective passages in the plate and the leg aligned. Guide pins 162 and 164 extend, respectively, through the respective aligned passages in the leg 112 and plate 160 and beyond the plate. These pins are so constructed and positioned as to be snugly received in guide bores in the surgical appliance of choice. A mounting screw 166 extends through the other of the three aligned passages and, in a preferred embodiment, is retained therein by a retainer nut, washer or keeper 168.

While two typical mounting means are shown and described in relation to the two exemplary embodiments shown, it will be apparent that the suture holder can be manufactured to incorporate any type of mounting means of any dimension. It is contemplated that holders will be made available that can be easily mounted on any type of surgical appliance which is amenable to supporting any suture holder or any device generally of the size of a suture holder. The suture holder can, of course, be made in any of several sizes to present sutures adjacent the surgical field by mounting the holder on a surgical appliance, on a table mount, from a ceiling mount, or in any other manner. Clearly, the nature of the mounting means is secondary and can be varied to meet any requirement.

To summarize, in a specific sense, without limiting the scope of the invention or the claims, the surgical suture holder may comprise a bracket constructed of generally planar bracket material having a thickness, the bracket being so configured and constructed as to define a first leg, having distal and proximal ends, for mounting the suture holder, a second leg, having distal and proximal ends, and a third leg, having distal and proximal ends, the proximal ends of the legs being joined together, the first leg extending between the second and third legs, the second and third legs each being so configured and constructed as to define therethrough at an elongate slot having a length and a width and having the depth which is the thickness of the bracket material. Prestressed coil springs each having a length and a diameter, the diameter of the springs being slightly less than the width of the slots in the bracket and being greater than the depth of the slots in the bracket are secured by suitable means in the respective slots with one longitudinal side portion of the respective springs extending outwardly from the surface of the bracket material a distance sufficient for sutures to be inserted between coils of the spring. The bracket, spring and spring securing means being so configured, constructed and assembled as to enable sutures to be inserted between spring coils against bias of one spring coil toward an adjacent coil to removably hold the suture in a position adjacent a surgical operating field for easy selection and removal by the surgeon or surgical assistant.

In one preferred form, the springs and bracket are so configured and constructed that the springs extends along the length thereof from the bracket a distance of from 1/16 inch to 1/4 inch. Typically, the thickness of the bracket is from about 3/32 to about 5/32 inch; however, none of these dimensions is critical.

It is preferred, but not critical that the spring securing means extend along the length of the respective springs adjacent thereto on a side opposite to the side of the spring that extends from the bracket. This latter structural relationship is clearly shown in FIG. 2, for example.

The suture holder of this invention is simple and certain in use. Surgical sutures, which may have the needles preattached, are simply laid over the suture holder spring and forced, by grasping suture or using a card or tool, between coils in the springs. The sutures can be arranged as desired and may be specially identified by location or otherwise; however, most sutures are identifiable by color. For example, the sutures may be placed in the order of expected use or by size, etc. The holder may be mounted to a surgical appliance, a bracket on the operating table or any other support device, or simply laid on the surgical drapes.

Within the concept of the invention and the appended claims there are many variations and adaptations of the suture holder of this invention. Configurations, materials and dimensions, for example, offer countless opportunities for manufacturing suture holders with the scope of the invention.

INDUSTRIAL APPLICATION

This invention is useful in the medical appliance and instrument industry.

What is claimed is:

1. A surgical suture holder comprising in combination:
   a bracket constructed of material having a thickness, the bracket being so configured and constructed as to define there through at least one elongate slot having a length and a width and having the depth which is the thickness of the bracket material;
   a coil spring having a length and a diameter, the diameter of the spring being slightly less than the width of the slot in the bracket and being greater than the depth of the slot in the bracket; and
   means securing the spring in the slot with one longitudinal side portion of the spring extending outwardly from the surface of the bracket a distance sufficient for sutures to be inserted between coils of the spring;
   the bracket, spring and spring securing means being so configured, constructed and assembled as to as to maintain the coils of the spring in conntact with rigid support structure for preventing the spring from bowing and to prevent sutures from wrapping around one or more coils of the spring, and to enable sutures to be inserted between spring coils against bias of one spring coil toward an adjacent coil to removably hold the suture in a position adjacent a surgical operating field for easy selection and removal by the surgeon or surgical assistant.

2. The invention of claim 1 further comprising means for mounting the suture holder to a surgical appliance.

3. The invention of claim 2 wherein the spring and bracket are so configured and constructed that the spring extends along the length thereof from the bracket a distance of from 1/16 inch to 1/4 inch.

4. The invention of claim 3 wherein the spring securing means extends along the length of the spring adjacent thereto on a side opposite to the side of the spring that extends from the bracket.

5. The invention of claim 4 wherein the bracket is so configured and constructed as to define two slots having a length and a width and having the depth which is the thickness of the bracket material, and comprises two prestressed coil springs each having a length and a diameter, the diameter of the springs being slightly less than the width of the slots in the bracket and being greater than the depth of the slots in the bracket and means securing the respective springs in the respective slots with one longitudinal side portion of the respective springs extending outwardly from the surface of the bracket a distance sufficient for sutures to be inserted between coils of the spring, each spring and spring securing means being so configured, constructed and assembled as to enable sutures to be inserted between spring coils against bias of one spring coil toward an adjacent coil to removably hold the suture in a position adjacent a surgical operating field for easy selection and removal by the surgeon or surgical assistant.

6. The invention of claim 1 wherein the spring and bracket are so configured and constructed that the spring extends along the length thereof from the bracket a distance of from 1/16 inch to 1/4 inch.

7. The invention of claim 6 wherein the spring securing means extends along the length of the spring adjacent thereto on a side opposite to the side of the spring that extends from the bracket.

8. The invention of claim 7 wherein the bracket is so configured and constructed as to define two slots having a length and a width and having the depth which is the thickness of the bracket material, and comprises two prestressed coil springs each having a length and a diameter, the diameter of the springs being slightly less than the width of the slots in the bracket and being greater than the depth of the slots in the bracket and means securing the respective springs in the respective slots with one longitudinal side portion of the respective springs extending outwardly from the surface of the bracket a distance sufficient for sutures to be inserted between coils of the spring, each spring and spring securing means being so configured, constructed and assembled as to enable sutures to be inserted between spring coils against bias of one spring coil toward an adjacent coil to removably hold the suture in a position adjacent a surgical operating field for easy selection and removal by the surgeon or surgical assistant.

9. The invention of claim 1 wherein the spring securing means extends along the length of the spring adjacent thereto on a side opposite to the side of the spring that extends from the bracket.

10. The invention of claim 9 wherein the bracket is so configured and constructed as to define two slots having a length and a width and having the depth which is the thickness of the bracket material, and comprises two prestressed coil springs each having a length and a diameter, the diameter of the springs being slightly less than the width of the slots in the bracket and being greater than the depth of the slots in the bracket and means securing the respective springs in the respective slots with one longitudinal side portion of the respective springs extending outwardly from the surface of the bracket a distance sufficient for sutures to be inserted between coils of the spring, each spring and spring securing means being so configured, constructed and assembled as to enable sutures to be inserted between spring coils against bias of one spring coil toward an adjacent coil to removably hold the suture in a position adjacent a surgical operating field for easy selection and removal by the surgeon or surgical assistant.

11. The invention of claim 1 wherein the bracket is so configured and constructed as to define two slots having a length and a width and having the depth which is the thickness of the bracket material, and comprises two prestressed coil springs each having a length and a diameter, the diameter of the springs being slightly less than the width of the slots in the bracket and being greater than the depth of the slots in the bracket and means securing the respective springs in the respective slots with one longitudinal side portion of the respective springs extending outwardly from the surface of the bracket a distance sufficient for sutures to be inserted between coils of the spring, each spring and spring securing means being so configured, constructed and assembled as to enable sutures to be inserted between spring coils against bias of one spring coil toward an adjacent coil to removably hold the suture in a position adjacent a surgical operating field for easy selection and removal by the surgeon or surgical assistant.

12. The invention of claim 11 further comprising means for mounting the suture holder to a surgical appliance.

13. The invention of claim 12 wherein the springs and bracket are so configured and constructed that the spring extend along the length thereof from the bracket a distance of from 1/16 inch to 1/4 inch and wherein the bracket is constructed of stainless steel plate from 3/32 inch to 5/32 inch thick.

14. A surgical suture holder comprising in combination:
a generally bracket constructed of generally planar bracket material having a thickness, the bracket being so configured and constructed as to define a first leg, having distal and proximal ends, for mounting the suture holder, a second leg having distal and proximal ends, and a third leg having distal and proximal ends, the proximal ends of the legs being joined together, the first leg extending between the second and third legs, the second and third legs bracket each being so configured and constructed as to define there through at an elongate slot having a length and a width and having the depth which is the thickness of the bracket material;

prestressed coil springs each having a length and a diameter, the diameter of the springs being slightly less than the width of the slots in the bracket and being greater than the depth of the slots in the bracket; and means securing the respective springs in the respective slot with one longitudinal side portion of the respective springs extending outwardly from the surface of the bracket a distance sufficient for sutures to be inserted between coils of the spring;

the bracket, spring and spring securing means being so configured, constructed and assembled as to enable sutures to be inserted between spring coils against bias of one spring coil toward an adjacent coil to removably hold the suture in a position adjacent a surgical operating field for easy selection and removal by the surgeon or surgical assistant.

15. The invention of claim 14 further comprising means for mounting the suture holder to a surgical appliance.

16. The invention of claim 15 wherein the springs and bracket are so configured and constructed that the springs extends along the length thereof from the bracket a distance of from 1/16 inch to 1/4 inch.

17. The invention of claim 16 wherein the spring securing means extend along the length of the respective springs adjacent thereto on a side opposite to the side of the spring that extends from the bracket.

18. The invention of claim 14 wherein the springs and bracket are so configured and constructed that the springs extends along the length thereof from the bracket a distance of from 1/16 inch to 1/4 inch.

19. The invention of claim 18 wherein the spring securing means extend along the length of the respective springs adjacent thereto on a side opposite to the side of the spring that extends from the bracket.

20. The invention of claim 14 wherein the spring securing means extend along the length of the respective springs adjacent thereto on a side opposite to the side of the spring that extends from the bracket.

21. A surgical suture holder comprising in combination:
a bracket constructed of material having a thickness, the bracket being so configured and constructed as to define there through at least one elongate slot having a length and a width and having the depth which is the thickness of the bracket material;

a coil spring having a length and a diameter the diameter of the spring being slightly less than the width of the slot in the bracket and being greater than the depth of the slot in the bracket; and means comprising a spring mounting bar for securing the spring in the slot with one longitudinal side portion of the spring extending, outwardly from the surface of the bracket a distance sufficient for sutures to be inserted between coils of the spring;

the bracket, spring and spring securing means being so configured, constructed and assembled as to as to maintain the coils of the spring in contact with the spring mounting bar for preventing the spring from bowing and to prevent sutures from wrapping around one or more coils of the spring and to enable sutures to be inserted between spring coils against bias of one spring coil toward an adjacent coil to removably hold the suture in a position adjacent a surgical operating field for easy selection and removal by the surgeon or surgical assistant.

22. A surgical suture holder comprising in combination:

a bracket constructed of material having a thickness, the bracket being so configured and constructed as to define there through at least one elongate slot, said slot having a length having edges extending there along, and a width and having the depth which is the thickness of the bracket material;, a coil spring having a length and a diameter, the diameter of the spring being slightly less than the width of the slot in the bracket and being greater than the depth of the slot in the bracket; and means securing the spring in the slot with one longitudinal side portion of the spring extending outwardly from the surface of the bracket a distance sufficient for sutures to be inserted between coils of the spring;

the bracket, spring and spring securing means being so configured, constructed and assembled as to as to maintain the coils of the spring in conntact with at least one of said edges of said slot for preventing the spring from bowing and to prevent sutures from wrapping around one or more coils of the spring, and to enable sutures to be inserted between spring coils against bias of one spring coil toward an adjacent coil to removably hold the suture in a position adjacent a surgical operating field for easy selection and removal by the surgeon or surgical assistant.

\* \* \* \* \*